United States Patent
Russo et al.

(10) Patent No.: US 9,611,140 B2
(45) Date of Patent: Apr. 4, 2017

(54) CONTROLLED FABRICATION OF NANOPORES IN NANOMETRIC SOLID STATE MATERIALS

(75) Inventors: Christopher John Russo, Cambridge (GB); Jene Golovchenko, Lexington, MA (US); Daniel Branton, Lexington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 94 days.

(21) Appl. No.: 14/004,743

(22) PCT Filed: Mar. 14, 2012

(86) PCT No.: PCT/US2012/029132
§ 371 (c)(1),
(2), (4) Date: Nov. 22, 2013

(87) PCT Pub. No.: WO2012/125770
PCT Pub. Date: Sep. 20, 2012

(65) Prior Publication Data
US 2014/0079936 A1    Mar. 20, 2014

Related U.S. Application Data

(60) Provisional application No. 61/452,704, filed on Mar. 15, 2011.

(51) Int. Cl.
*G01L 21/30* (2006.01)
*B81C 1/00* (2006.01)
*G01N 33/487* (2006.01)

(52) U.S. Cl.
CPC ... *B81C 1/00087* (2013.01); *G01N 33/48721* (2013.01); *B81B 2201/0214* (2013.01); *B81B 2203/0127* (2013.01); *B81B 2207/056* (2013.01)

(58) Field of Classification Search
CPC .......... B81C 1/0087; B81B 2203/0127; G01N 33/48721; H01L 2224/2763; H01L 21/2605; H01L 21/26566
(Continued)

(56) References Cited

U.S. PATENT DOCUMENTS

| | | |
|---|---|---|
| 2004/0149580 A1 | 8/2004 | Flory |
| 2006/0278580 A1* | 12/2006 | Striemer ................ B01D 61/18 |
| | | 210/650 |

(Continued)

FOREIGN PATENT DOCUMENTS

| | | |
|---|---|---|
| CN | 101694474 | 4/2010 |
| WO | 2009035647 | 3/2009 |

(Continued)

OTHER PUBLICATIONS

PCT/US2012/029132, International Search Report, PCT/ISA/210, first sheet, second sheet pp. 1-2, and patent family annex, Oct. 2012.

(Continued)

*Primary Examiner* — Binh X Tran
(74) *Attorney, Agent, or Firm* — Theresa A. Lober

(57) ABSTRACT

In a method of forming a nanopore in a nanometric material, a nanopore nucleation site is formed at a location that is interior to lateral edges of the nanometric material by directing a first energetic beam, selected from the group of ion beam and neutral atom beam, at the interior location for a first time duration that imposes a first beam dose which causes removal of no more than five interior atoms from the interior location to produce at the interior location a nanopore nucleation site having a plurality of edge atoms. A nanopore is then formed at the nanopore nucleation site by directing a second energetic beam, selected from the group consisting of electron beam, ion beam, and neutral atom beam, at the nanopore nucleation site with a beam energy (Continued)

that removes edge atoms at the nanopore nucleation site but does not remove bulk atoms from the nanometric material.

20 Claims, 5 Drawing Sheets

(58) Field of Classification Search
USPC .................................... 216/60, 65, 66, 81
See application file for complete search history.

(56) References Cited

U.S. PATENT DOCUMENTS

| | | | |
|---|---|---|---|
| 2007/0080107 A1* | 4/2007 | Yang ............... | B01D 67/0034 210/490 |
| 2011/0048947 A1* | 3/2011 | Petronis ........... | B01D 67/0062 204/483 |
| 2011/0266521 A1* | 11/2011 | Ferrari ............. | B82Y 30/00 257/14 |
| 2012/0037919 A1* | 2/2012 | Xu .................. | B82Y 15/00 257/76 |
| 2014/0262820 A1 | 9/2014 | Kuan et al. | |

FOREIGN PATENT DOCUMENTS

| | | |
|---|---|---|
| WO | 2009045472 | 9/2009 |
| WO | 2011143340 | 11/2011 |

OTHER PUBLICATIONS

PCT/US2012/029132, Written Opinion of the International Searching Authority, PCT/ISA/237, cover sheet, Written Opnion sheet, and Separate Sheet 1—Separate Sheet 3, Oct. 2012.
Sint et al., "Selective Ion Passage through Functionalized Graphene Nanopores," J. Am. Chem. Sco. vol. 130, pp. 16448-16449, Nov. 2008.
Girit et al., "Graphene at the Edge: Stability and Dynamics," Science, vol. 323, pp. 1705-1708, Mar. 2009.
Meyer et al., "Selective Sputtering and Atomic Resolution Imaging of Atomically Thin Boron Nitride Membranes," Nano Letters, vol. 9, No. 7, pp. 2683-2689, 2009.
Chinese Patent Application No. 201280023390.3, First Office Action, pp. 1-4, Text of First Office Action, pp. 1-8, Apr. 2015.
Chinese Patent Application No. 201280023390.3, Response to First Office Action, pp. 1-12, Aug. 2015.
European Patent Application No. 12710848.8-1508, First Office Action, pp. 1-2, claims pp. 31-36, Nov. 2013.
European Patent Application No. 12710848.8-1508, response to First Office Action, pp. 1-8, claims pp. 1-3 and pp. 1-5, May 2014.
Australian Patent Application No. 2012229925, Patent Examination Report No. 1, pp. 1-4, Dec. 2014.
Australian Patent Application No. 2012229925, Response to Patent Examination Report No. 1, pp. 1-11, Aug. 2015.
Fischbein et al., "Electron beam nanosculpting of suspended graphene sheets," Appl. Phys,. Letts., vol. 93, pp. 113107-1-113107-3, 2008.
Healy et al., Solid-state nanopore technologies for nanopore-based DNA analysis, Future Medicine, vol. 2, No. 6, pp. 875-897, 2007.
Japanese Patent Application No. 2013-558153, claim amendments, pp. 1-6, Mar. 2015.
Japanese Patent Application No. 2013-558153, First Examiner Action, pp. 1-3, 2015.
Japanese Patent Application No. 2013-558153, Examiner Action including claim listing, p. 1-7, Oct. 27, 2015.
Japanese Patent Application No. 2013-558153, Response to Examiner Action, p. 1-2, claims amendments, p. 1-5, Jan. 15, 2016.
Australian Patent Application No. 2012229925, Patent Examination Report No. 2, pp. 1-4, Sep. 3, 2015.
Australian Patent Application No. 2012229925, Response to Patent Examination Report No. 2, pp. 1-6, Nov. 10, 2015.
Chinese Patent Application No. 201280023390.3, Second Office Action, pp. 1-5, Dec. 7, 2015.
Chinese Patent Application No. 201280023390.3, Response to Second Office Action, p. 1, Claims, pp. 1-5, Feb. 22, 2016.
Japanese Patent Application No. 2016-046487, Examiner Action, p. 1-6, claims under examination pp. 1-2, Oct. 11, 2016.
Australian Patent Application No. 2016201323, Patent Examination Report No. 1, pp. 1-3, claims under examination pp. 1-2, Aug. 19, 2016.

\* cited by examiner

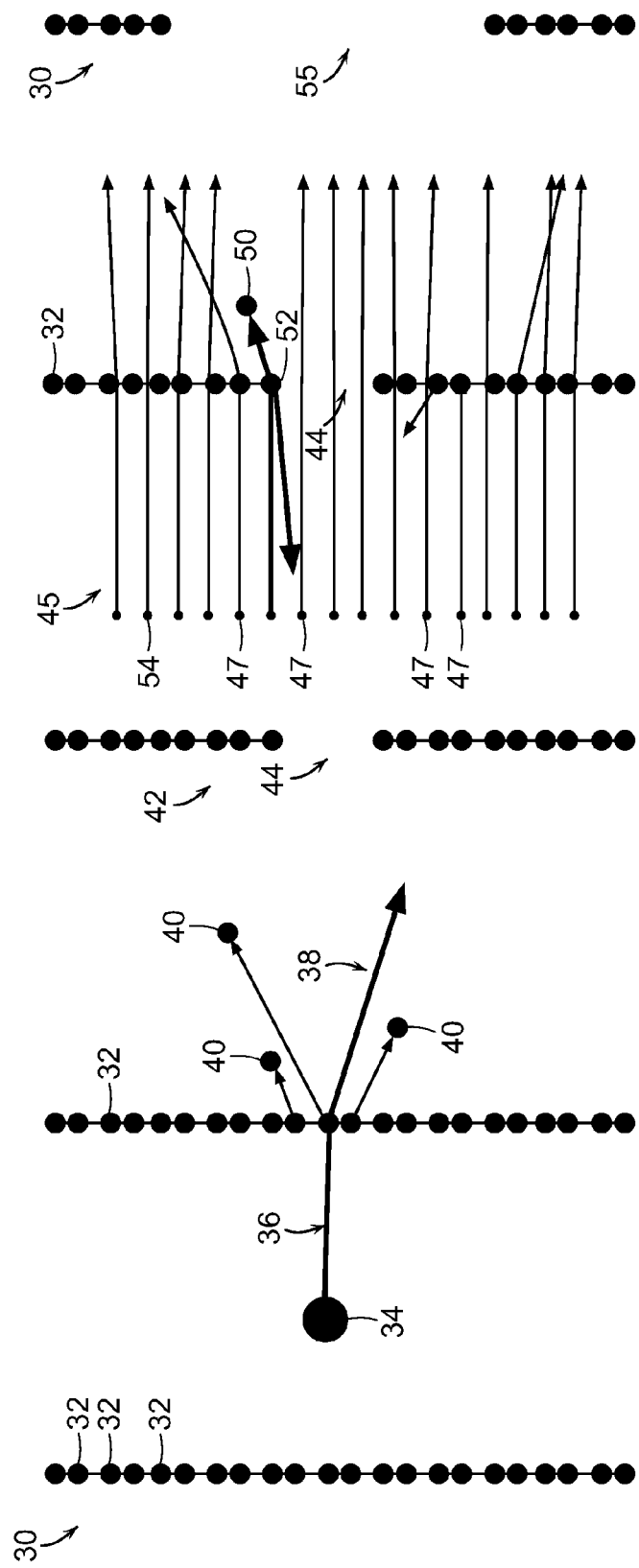

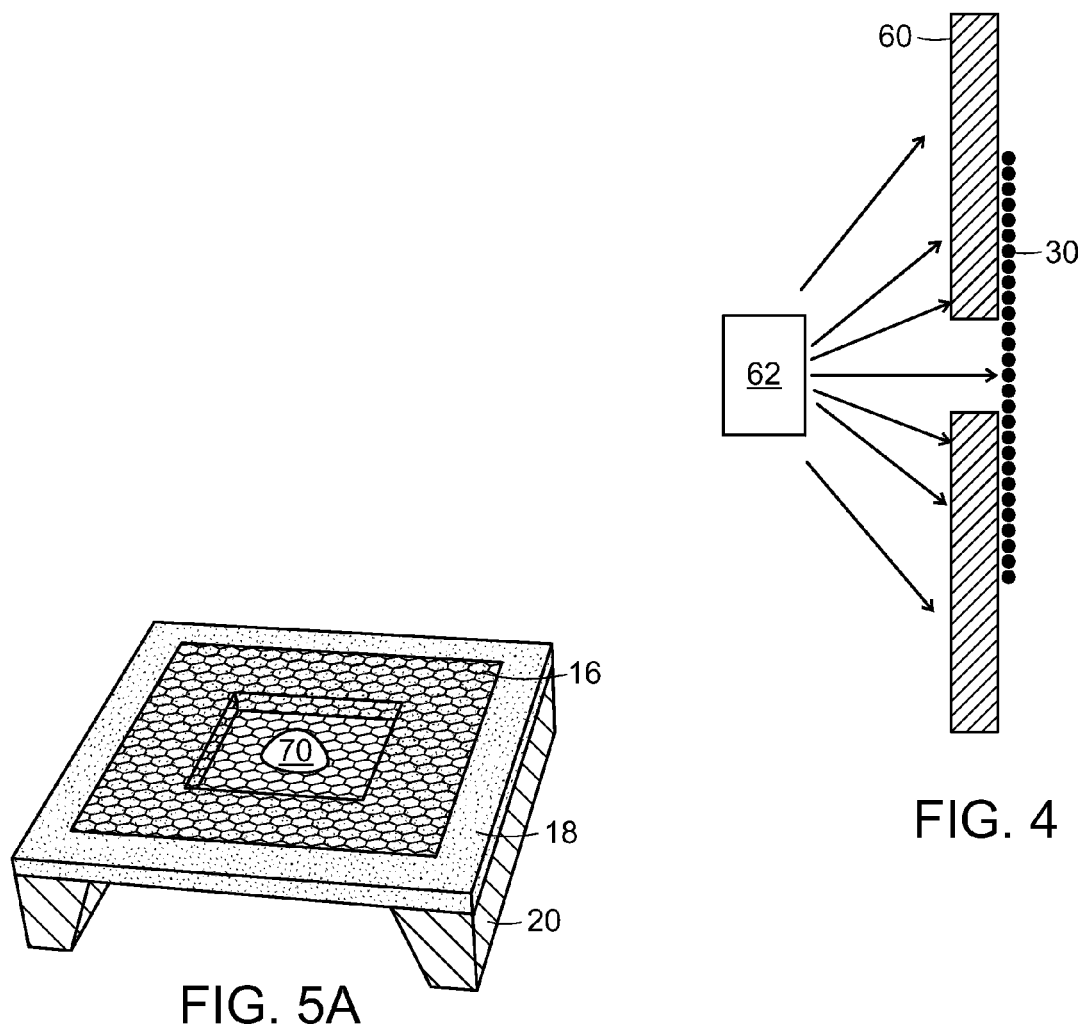
FIG. 4
FIG. 5A
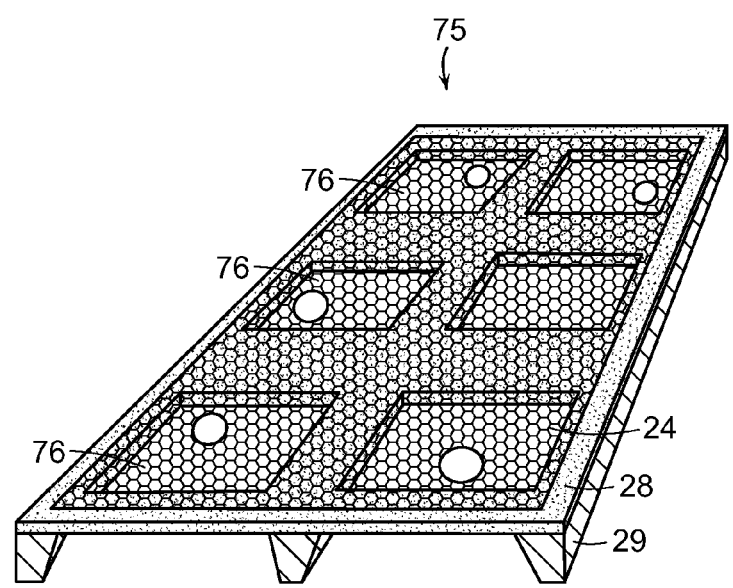
FIG. 5B

CONTROLLED FABRICATION OF NANOPORES IN NANOMETRIC SOLID STATE MATERIALS

CROSS-REFERENCE TO RELATED APPLICATIONS

This application claims the benefit of U.S. Provisional Application No. 61/452,704, filed Mar. 15, 2011, the entirety of which is hereby incorporated by reference.

STATEMENT REGARDING FEDERALLY SPONSORED RESEARCH

This invention was made with Government support under Contract No. R01HG003703, awarded by the National Institutes of Health. The Government has certain rights in the invention.

BACKGROUND

This invention relates generally to nano-scale fabrication techniques, and more particularly relates to techniques for producing nanopores in nanometric solid state materials.

Nanometric solid state materials, that is, solid state materials that can exist in equilibrium with only nanometers in thickness, include a wide range of materials such as monolayer, few-monolayer, and single molecule materials, that are becoming increasingly important for a wide range of applications, including, e.g., electronic, biological, and chemical applications. Many such applications require high-precision nanoscale features and structures for operation. For example, well-defined nanopores, or nanoscale pores having a diameter less than about 100 nanometers, are particularly required for many applications due to the nano-scale of the application itself or the environment in which the nanopore is to operate.

For example, nanopore-articulated nanoscale devices are of great interest for enabling the localization, detection, and characterization of molecules such as single DNA molecules or protein molecules. Nanopore filters and nanoscale holey membranes are likewise important for many critical biological separation and characterization procedures, as well as filtration processes. Many other micro-fluidic and nano-fluidic processing and control applications similarly rely on nano-scale features in nanometric materials.

To produce a nanoscale structure such as a nanopore in a nanometrically-thin material, it is in general required to manipulate the material with the precision of single atoms. This is in contrast to most conventional microelectronic fabrication processes, which characteristically only require precision that approaches the micron-scale. But without feature resolution and fabrication precision at the atomic level, it has in general not been possible to manipulate nanometrically-thin materials in a manner that exploits the particular characteristics which emerge at the nano-scale.

High-precision nanoscale processing has historically required a one-at-a-time fabrication paradigm that is often costly and inefficient. Generally, the high-volume, batch fabrication techniques of conventional microelectronic production have been incompatible with nanoscale feature production and material manipulation. But without the ability to precisely, reproducibly, and inexpensively mass-produce nanoscale features such as nanopores, many nanoscale systems cannot be developed for commercial implementation of many important nanoscale applications.

SUMMARY OF THE INVENTION

There is provided a method and corresponding structures that overcome the limitations of previous processes to controllably form nanopores. In one example method of forming a nanopore in a nanometric material, a nanopore nucleation site is formed at a location of the nanometric material that is interior to lateral edges of the material by directing a first energetic beam, selected from the group of ion beam and neutral atom beam, at the interior location for a first time duration that imposes a first beam dose which causes removal of no more than five interior atoms from the interior location to produce at the interior location a nanopore nucleation site having a plurality of edge atoms. A nanopore is then formed at the nanopore nucleation site by directing a second energetic beam, selected from the group consisting of electron beam, ion beam, and neutral atom beam, at the nanopore nucleation site with a beam energy that removes edge atoms at the nanopore nucleation site but does not remove bulk atoms from the nanometric material.

With this method, there can be produced a nanometric structure with nanopores. The structure is formed of an impermeable self-supporting nanometric material having a thickness of no greater than about 5 nm. In the nanometric material is a plurality of nanopores of at least about 1000 nanopores/cm². Each of the nanopores has a diameter that is no greater than about 10 nm. The plurality of nanopores is monodisperse in diameter with a variation of about ±30%.

This nanometric structure of nanopores, and the method for producing the nanopores, enables a wide range of micro-fluidic and nano-fluidic applications, including molecular detection and analysis, fluidic filtering and separation, and fluidic reactions.

Other features and advantages will be apparent the following description and accompanying figures, and from the claims.

BRIEF DESCRIPTION OF THE DRAWINGS

FIGS. 3A-3E are schematic side views of a nanometric material as the nanometric material is processed in the steps of the flow chart of FIG. 1;

FIG. 4 is a schematic side view of a patterned shielding material employed to selectively mask a nanometric material during the nanopore fabrication process of the flow chart of FIG. 1;

FIGS. 5A-5B are schematic views of nanopores formed in nanometric materials disposed across an opening on a support frame and disposed across an array of openings on a support frame, respectively, produced by the method of the flow chart of FIG. 1;

DETAILED DESCRIPTION

Figure 1:
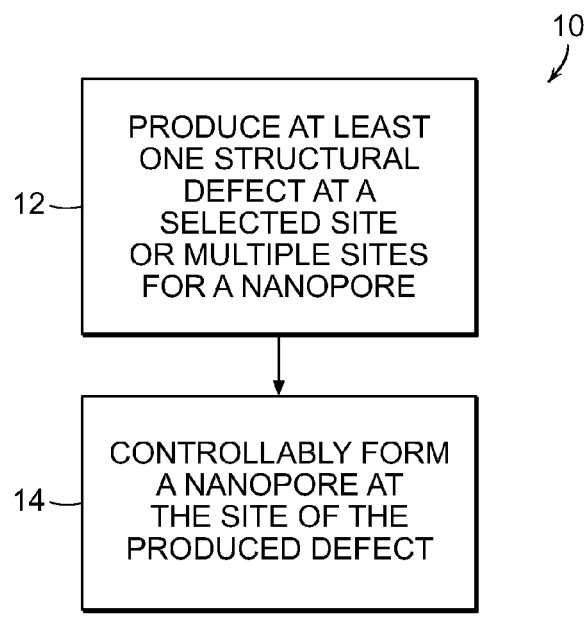
FIG. 1 is a flow chart of a two-step process for producing a nanopore in a nanometric material.

Referring to FIG. 1, a process 10 for controllably forming one or more nanopores can in general be implemented in a nanometric material with the two steps shown therein. In a first step 12, at least one nanopore nucleation site is produced at a selected location or at multiple selected locations in a nanometric material for which the controlled fabrication of a nanopore is desired. Then in a second step 14, a nanopore is controllably formed at the nucleation site or sites. Each of these steps is described in detail below.

This two-step nanopore formation method can be applied to any suitable material, but is particularly well-suited for producing nanopores in a solid state material or structure that is characterized by a thickness that is nanometric, and for many applications, that is less than about 5 nanometers in thickness or less than 3 nanometers in thickness. Such nanometric materials include, e.g., atomically-thin materials, which in general can be described as materials having a thickness of an atomic monolayer or a few atomic layers, such as a monolayer, a bilayer, or a trilayer of atoms. A mono-atomically-thick material is herein defined as a material which is one atom in thickness, but need not be atoms of just one element. Atoms of a plurality of different elements can be included in an atomic layer. The mono-atomically-thick layer can be decorated at the layer top and/or bottom with heterogeneous atoms and other species that do not lie in the plane of the atoms. Such atomically-thin materials include, e.g., two-dimensional free-standing atomic crystals, and other structures having a characteristic unit, like a lattice constant, that is repeating in two dimensions but not the third. Atomically-thin materials also include non-crystalline materials, such as glassy materials for which a mono-atomic layer and few-atomic-layers can be formed. Other example nanometric materials include materials that are a single molecule in thickness, or that are two or three molecules in thickness.

Examples of nanometric materials that are well-addressed by the method include graphene, few-layer graphene, fluorographene, graphane, graphene oxide, hexagonal boron nitride (hexagonal-BN), mono-atomic glasses, and other such materials. Other suitable materials include, e.g., $MoS_2$, $WS_2$, $MoSe_2$, $MoTe_2$, $TaSe_2$, $NbSe_2$, $NiTe_2$, $Bi_2Sr_2CaCu_2O_x$, and $Bi_2Te_3$. These are representative examples of suitable nanometric solid state materials but are not limiting; any suitable material in which one or more nanopores are to be formed can be employed.

In the method, a selected nanometric material is provided in a suitable configuration for processing to produce one or more nanopores in the material. The nanometric material is preferably arranged such that one or more energetic species can be directed through the material for both producing a nanopore nucleation site and for controllably forming a nanopore at the site, as explained in detail below. For many applications, it can be convenient to arrange the nanometric material on a continuous or discontinuous underlying support structure in any convenient orientation that accommodates such nanopore processing. The support structure can be discontinuous, with a topology and material configuration depending on an intended application, and can serve as a masking material, patterned with, e.g., openings of a selected masking pattern, as described below. The nanometric material in which a nanopore is to be formed can be, e.g., self-supporting, with support at lateral edges near or at the periphery of the material or at locations within at interior points, or in another configuration that accommodates the direction of an energetic species through the nanometric material. The nanometric material can be synthesized in-position, e.g., in situ in a device or system configuration, on a selected support structure, or can be produced or synthesized fully or partially elsewhere and then transferred to the selected support structure.

The support structure can be provided as any suitable support material, including microelectronic materials and substrates that are electrically conducting or electrically insulating. The support structure can be provided as a bulk structure having the composition of the nanometric material or can be provided as a heterogeneous combination of materials. In one example, a support structure is provided as a frame and the nanometric material in which one or more nanopores are to be produced is transferred to the frame.

Figure 2A:
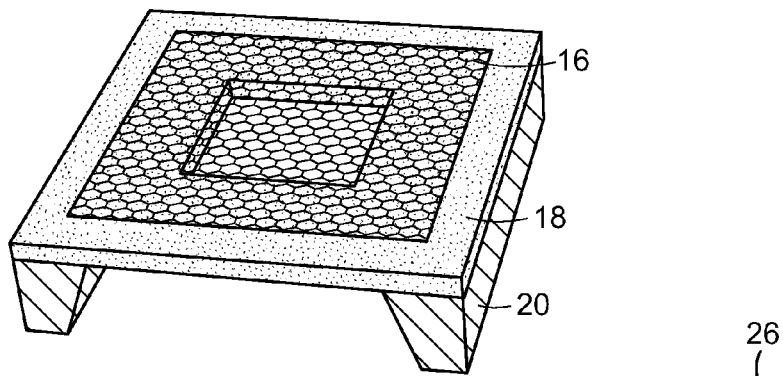
FIGS. 2A and 2B schematic views of nanometric materials disposed across an opening on a support frame and disposed across an array of openings on a support frame, respectively, for carrying out the method of the flow chart of FIG. 1.
Figure 2B:
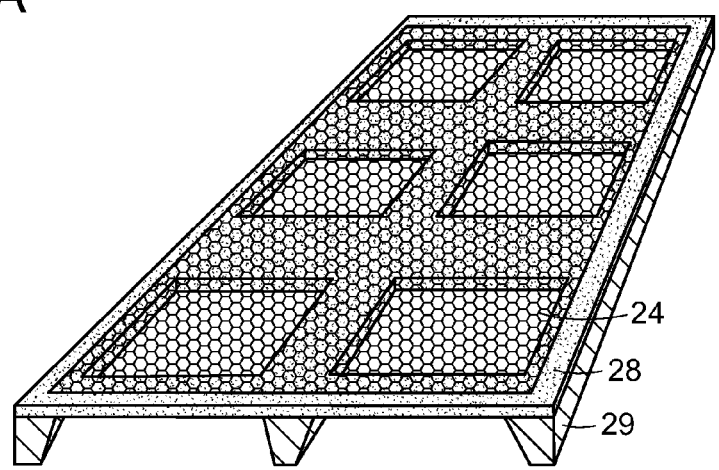

For example, a silicon substrate can be configured as a support with a frame membrane, e.g., a silicon nitride or other material frame membrane, having one or more apertures in the frame membrane. As shown in FIG. 2A, the nanometric material 16 can be positioned over the frame membrane 18 on the substrate 20. The frame membrane 18 thereby operates as a support frame around the aperture 22, to enable a self-supported region 24 of nanometric material across the aperture 22. As shown in FIG. 2B, this arrangement can be extended to accommodate any number of distinct areas of nanometric material that are each suspended 24 in an array 26, disposed in a support frame 28 across apertures in the frame membrane on a substrate.

In general, the apertures provided in a support frame membrane layer can be, e.g., rectangular, circular, or of another suitable geometry, and can be, e.g., between about 5-10 nm and about 200 nm in extent or other geometry and extent corresponding to a selected nanopore size and location, as explained in more detail below. For many applications, it can be preferred that the aperture in the support frame membrane be at least about ten times greater than the nanopore to be formed in the nanometric material.

In a further example, a transmission electron microscopy (TEM) grid can be employed as a support frame for a nanometric material to be processed. The TEM grid can be covered with a suitable material, such as a thin amorphous carbon film, and one or more holes, or an array of holes, can be formed in the film to provide a frame for the nanometric material. Other such arrangements can be employed and no particular support or frame is required.

Where the nanometric material is synthesized separately from a support or frame, the material can be transferred to a support or frame at a convenient juncture in the synthesis process. In one example, a single layer of graphene or few-layer graphene is synthesized and once synthesized, is transferred to a selected support structure. In this example, the graphene can be synthesized by a suitable process, e.g., a chemical vapor deposition process (CVD), or by ion implantation or gas phase synthesis, or by another synthesis technique on a suitable structure, e.g., a metal layer or substrate, or can be produced by exfoliation of graphite, in the conventional manner. Alternatively, the material can be synthesized by a suitable process, e.g., (CVD), ion implantation, or another synthesis technique, on a suitable structure, e.g., a metal layer or substrate, after which the structure, e.g., a metal layer or substrate, can be converted into a support structure for the nanometric material by some method, such as a patterned chemical etching, that does not affect the nanometric material through which nanopores are subsequently to be formed. No particular nanometric material synthesis process is required, and the nanometric material to be processed, such as graphene, can be produced in any suitable manner.

In one particularly convenient graphene synthesis process, a nickel or copper foil can be annealed at a low pressure at a temperature of, e.g., about 1000° C., for about 10 minutes, under the flow of $H_2$, and then also exposed to flow of $CH_4$ for about 10 minutes at 1000° C., to grow a region or regions of graphene. At the end of the 10 minute growth step, the foil is cooled to room temperature with flow of $H_2$, in a process which takes about 2 hours.

If the nanometric material to be processed is produced on a synthesis structure, such as the graphene synthesis on copper foil just described, then it is preferred that the nanometric material be well-cleaned and, if the nanometric material is to be transferred, that this transfer proceed with great care so as not to damage or contaminate the nanometric material. For example, once graphene is synthesized on a copper foil, a suitable piece of graphene on the foil can be punched out and placed on an acid-washed clean glass slide for handling during transfer to a support structure. Polymer-based handle materials can alternatively be employed. Where the support structure is, e.g., a TEM grid having a holey carbon layer, a droplet of deionized water or other suitable liquid is first placed on the grid layer, and then when brought into contact with the graphene, the carbon film is pulled into intimate contact with the graphene by the receding interface from the liquid. A glass slide can be placed on top of the TEM grid to enable application of force during the contact.

The copper film on which the graphene was synthesized can then be etched away from below by, e.g., floating the structure on a suitable etchant, e.g., a copper etchant including $FeCl_3$ for a suitable duration, e.g., 15 minutes for a 25 µm-thick foil. If over-etched, the $FeCl_3$ will attack the TEM grid at locations where the grid is exposed at carbon layer edges. Similarly, a polymer film can be removed after placement of the graphene. Once the copper film or other material is removed, the graphene as-positioned on the TEM grid can be cleaned, e.g., by floating the structure in 1 N HCl, to remove residual iron from the $FeCl_3$ exposure, for about 10 minutes, and then floated in multiple rinses of deionized water, for example, about three rinses of ten minutes each, to remove any residual salt, and dried in dry nitrogen.

For many nanometric materials in which a nanopore is to be formed, e.g., graphene, a high degree of cleanliness is especially preferred, specifically, with regard to graphene, e.g., to reduce the density of hydrocarbon contaminants such that mobile hydrocarbons on the graphene surface are substantially reduced. This high degree of cleanliness can be preferred for aiding in the nanopore formation process. Therefore, if after the cleaning and rinsing process described above it is found that some amount of surface contamination remains, it can be preferred to conduct a further cleaning step.

In one example cleaning process, contaminants are baked out of the structure. Here the TEM grid with, e.g., a graphene layer affixed as described above, is transferred to a stainless steel ultra high vacuum (UHV) chamber, and at a pressure of, e.g., less than about $10^{-8}$ Torr, the temperature is ramped to about 300° C. The structure is then baked for at least two hours, and preferably overnight, at this temperature. The chamber is then cooled to room temperature slowly, e.g., at less than about 2° C./min, with a final chamber pressure at between, e.g., about $10^{-8}$ T and about $10^{-9}$ T. It is preferred that the structure be stored at room temperature under UHV conditions until use. This process is found to produce a graphene surface that is about 40%-80% free of any contaminating material, as-observed by TEM viewing.

This example demonstrates that in general, it is preferred to maintain the nanometric material to be processed under optimally clean conditions, so that atomic-scale processing of the material is not affected by contaminants. No particular cleaning or storage processes are required, and those processes best-suited to a selected material are preferred. With a selected material in place on a support structure, the method for controllably producing a nanopore can be carried out.

Referring to FIG. 3A, there is shown a nanometric material 30 to be processed for the production of nanopores, arranged such that a plane of atoms 32 of the material is accessible. In this example illustration, one layer of atoms is shown for clarity in explaining the process steps, but such is not required; as explained above, the nanometric material can be an atomic multilayer material, a molecular monolayer material, or other nanometric material having a thickness that is generally less than about 5 nm.

With the nanometric material in such an arrangement, in the first method step, one or more nanopore nucleation sites are formed in the nanometric material at locations that are interior to the lateral edges of the nanometric material, and at which nanopores are to be formed. At such an interior nanopore nucleation site, some disruption to the continuity of the nanometric material is provided that produces edges of material from which edge atoms can be removed for controllably forming a nanopore of a selected size. In other words, due to a disruption in the nanometric material, interior atoms are rendered as edge atoms for removal in the process of forming a nanopore. Each nanopore nucleation site is therefore a site at an interior location of the nanometric material where edge atoms are produced by the nucleation site formation.

To form a nanopore nucleation site, some perturbation of the nanometric material atoms is required. In one example of such, a structural defect or a single cluster of defects is formed in the nanometric material at a location interior to lateral edges of the material. The defect can be created by, e.g., displacing a single atom or small number of atoms in the material or otherwise disrupting the atomic structure of the material. The term "defect" is therefore here intended to refer to an aberration in the atomic bonding structure of the nanometric material. For example, given the nanometric material graphene, a defect can be created by the removal of one or two atoms from the $sp^2$ bonded graphene carbon network of the material. A sufficient defect exists in the material when the number of bonds holding one or more atoms in place is altered and/or reduced and the defect is relatively stable at a selected operating temperature. A one or two atom defect in a hexagonal lattice such as that of graphene can produce three-four edge atoms at the site of the defect, and therefore enables the requisite condition of the production of edge atoms at an interior nanometric material location for a nanopore nucleation site.

In general, the disruption to the nanometric material at the nucleation site can be produced in any suitable manner. In one preferable example, an energetic beam of a selected particle species is directed to a location or locations on the surface of the nanometric material that is selected for production of a nanopore. An ion beam, e.g., a beam of argon ions, an α-particle beam, a high-energy beta particle beam, an electron/proton beam, a reactive ion beam created by a plasma, such as an oxygen ion or free radical, or other suitable beam of particles can be employed. For many applications, an ion beam or beam of neutral atoms can be preferred for ease of use in conventional microfabrication batch processing sequences. Example suitable energetic beams include, e.g., He ion beams, hydrogen/proton beams, neon beams, and gallium ion beams, among other suitable species. The energetic beam is not required to itself directly knock out one or more atoms from the nanometric material; the energy delivered by the beam can cause a disruption in atomic bonding that displaces one or more atoms.

Therefore, the energy of the particle beam is characterized as being above that energy which provides a minimum particle recoil energy required to remove at least one atom from the interior of a nanometric lattice, called the displacement energy, $E_d^{bulk}$. In other words, there must be provided by the particle beam a minimum threshold kinetic energy for the incident particle to displace one or more interior atoms, such that a nanopore nucleation site is produced, or can otherwise directly and irreversibly break the bonds of the substituent lattice.

$T_m$, the maximum transmitted energy in a single recoil scattering event, occurs with a direct head on collision by an incident particle from the beam; in a relativistic formulation, this transmitted energy is given as:

$$T_m = \frac{2ME(E + 2m_0 c^2)}{(M + m_0)^2 c^2 + 2ME} \quad (1)$$

where E is the minimum energy of the beam required to create a nanopore nucleation site by removal of an atom, $m_0$ is the incident particle mass at rest, c is the speed of light, and M is the mass of the atom to be removed from the lattice.

A simple estimate for the displacement energy, $E_d^{bulk}$, of a particular atom within the bulk lattice of a given material is obtained by summing the energy of all of the bonds in the lattice, based on, e.g., tabulated values. For example, the estimated displacement energy for a carbon atom in a monolayer of graphene using this method is $E_d^{bulk} \approx 6.4$ eV×3=19 eV, a value that is reasonably close to the measured values for graphene in bulk graphite of 20-21 eV. Note that the displacement energy is a function of the angle between the incident beam and the plane of the atoms in the lattice. In this analysis, it can be assumed that the beam is substantially perpendicular to the nanometric material plane. The minimum energy of the beam, E, to create a defect can then be calculated using Expression (1) above with $T_m$ set to the displacement energy, $E_d^{bulk}$, plus some margin of error to account for the uncertainty of the beam energy in the apparatus and the approximate nature of the calculation, say 50%.

For a beam of low energy ions, having a kinetic energy that is much less than the rest energy, employed to produce nanopore nucleation sites, in which case a non-relativistic analysis applies, Expression (1) simplifies to:

$$E = T_m \frac{(m_0 + M)^2}{4m_0 M} \quad (2)$$

Based on this expression, it can be specified that for a beam of low-energy ions, an appropriate beam energy to remove atoms for producing in a nanometric material nanopore nucleation sites, $E_{nuc}$, including a 50% margin of error, is given as:

$$E_{nuc} \geq 1.5 \cdot E_d^{bulk} \frac{(m_0 + M)^2}{4m_0 M} \quad (3)$$

Based on this Expression (3) above, and given estimates of $E_d^{bulk}$ using the method above, there can be determined the requisite beam energies for a beam of interest. For example, given an argon ion beam, Table 1 below specifies the requisite beam energy for nanopore nucleation site formation for three nanometric materials.

TABLE 1

| Target material | Bulk atom displacement energy estimate $E_d^{bulk}$ | Argon beam energy for nanopore nucleation $E_{nuc}$ |
| --- | --- | --- |
| Graphene | 21 eV | >44 eV |
| Boron nitride | B = 15 eV N = 14 eV | >34 eV |
| Molybdenum disulfide | Mo = 10 eV S = 5.2 eV | >19 eV |

In most metallic and semi-metallic materials which are not subject to other forms of irradiation-induced damage, below the requisite beam energy, impinging beam particles do not damage a pristine lattice, even after very large doses of irradiation. For example, a pristine graphene lattice can withstand a dose of >$10^9$ electrons/nm$^2$ at 80 keV without any damage to the lattice.

For many applications, the minimum incident beam energy required to produce nanopore nucleation sites can be determined empirically. For example, a selected nanometric material can be irradiated with an energetic beam at an initial energy for which $T_m$~5 eV. Then the energy of the beam can be slowly increased until there is evidence that atoms of the nanometric material are being removed by the beam. This experiment can be conducted all on one nanometric material sample if a detector is available to in situ detect recoiling atoms from the material. Alternatively, this experiment can be conducted on several different nanometric material samples, with stepwise increases in energy and a post imaging step to determine that atoms were removed. Once an appropriate energy is determined for a given incident particle/material combination, then the dose required to remove a particular number of atoms per unit area can also be measured and then specified a priori to create a desired number of nucleation sites per unit area on a selected nanometric material.

Once a beam energy is selected, then the duration of exposure of the nanometric material to the energetic beam is selected to produce the desired nanopore nucleation site. Specifically, the duration of time during which the energetic beam is directed at the nanometric material location or locations is set to impose a dose of particles from the beam that produces a nanopore nucleation site. Preferably, the nanopore nucleation site is controlled to be of atomic-scale dimensions. The nucleation site, for most applications, can be therefore be specified as a location in the nanometric material that is interior to lateral edges of the nanometric material and at which about five or less interior atoms have been removed by the energetic beam. The dose of particles from the energetic beam thereby produces a nucleation site at the interior of the nanometric material at which five or less interior atoms have been removed, producing a plurality of edge atoms at the site. For example, given the nanometric material graphene, an argon ion beam dose of about $1\times10^{13}$ $Ar^+/cm^2$ at a beam energy of about 3 keV can be employed to produce nanopore nucleation sites in the graphene. With this control of nanopore nucleation site production, the continuity of the nanometric material is disrupted by the removal of five or less atoms, at an interior location, so that interior atoms at the site are rendered as edge atoms, for formation of a nanopore.

Under some processing conditions and for some materials such as graphene, there is demonstrated a resistance by the nanometric material to form a nanopore nucleation site at room temperature, even above the knock on threshold, due to mobility of atoms in the nanometric material. As a result, it can be preferred to experimentally determine the characteristic tendency of a selected nanometric material to be disrupted at a selected operating temperature, and to cool the material during irradiation, if necessary, to preserve the disruption in the material. For example, graphene cooled to 149 K and irradiated by 3 keV $Ar^+$ is damaged with defects appropriate for making nanopores but graphene that is irradiated by 3 keV $Ar^+$ ions at 300 K shows far fewer nanopore nucleation sites. Specifically, at 300 K the probability that a single argon ion will produce a defect for nucleation of a nanopore is $<1/10^{th}$ of that probability at 148 K.

It is therefore desirable to cool the nanometric material to a temperature that reduces surface ad-atom diffusion such that mobile atoms cannot replace atoms removed by the incident energetic beam. Based on measurements of irradiation of graphite, this temperature is understood to be in the range of about 160 K-200 K for graphene. As a result, a processing temperature below about 200 K can be preferred, and a temperature below about 160 K can be more preferred, with lower temperatures improving the efficiency of nanopore nucleation site creation. It is to be understood that this temperature can vary for different nanometric materials. The appropriate processing temperature for a given nanometric material can be determined empirically by reducing the temperature of the nanometric material during energetic beam irradiation until the nanopore nucleation site creation efficiency becomes comparable to the cross section for atomic displacement.

The production of a nanopore nucleation site in a nanometric material by an incoming particle is schematically shown in FIG. 3B. A particle 34 in a beam of particles is directed 36 to the nanometric material. The collision of each such particle 34 with atoms 32 of the material can remove one or a number of atoms in a single collision, with the removed atoms 40 taken out of the nanometric material structure as the particle traverses and exits 38 the nanometric material. As shown in FIG. 3C, this results in a changed nanometric material 42, now including a nanopore nucleation site 44 having an edge at which edge atoms can be removed.

The dose of the nanopore nucleation-generating particles can be controlled such that only one isolated material disruption or one cluster of disruptions is created at a nanopore site of a nanometric material or at each of a plurality of sites of interest. This can be achieved, e.g., using a calibrated source for an accurately-controlled beam irradiation duration, or for a liquid environment, e.g., feed-back control from ionic currents that can be provided, for example, by monitoring ionic flow through a material, such as a sheet of graphene, that is suspended so as to separate two ion containing solutions, one of which is biased with respect to the other.

With this control, the nanometric material being processed can be positioned with respect to the nanopore nucleation site-generating particles so that one material disruption or one cluster of disruptions is produced at a location that is specified for formation of a nanopore, or so that an array of material disruptions is produced across the material for formation of an array of nanopores in the material. Where more than one nanopore is desired, a physical masking arrangement can be employed to expose only those locations of the nanometric material at which nanopores are to be formed to the disrupting environment. Here, e.g., as shown in FIG. 4, a patterned shielding mask 60 of sufficient thickness and of appropriate material to prevent penetration of particles can be positioned in front of the nanometric material 30 so that a source of particles, whether focused or unfocused, as shown, will irradiate only a selected region or regions of the nanometric material.

Many materials have stopping power to a beam of ions that is sufficient for operation as a relatively thin ion beam mask. For example, a thin foil of Al, Au, Si, Cu, $SiO_2$, $SiN_x$, nylon, Teflon, or other suitable material can be employed. In a further example, it is found that alpha particles resulting from radioactive decay have a very low penetration depth, a few centimeters of air, and therefore can be stopped by a few-micrometer layer of aluminum foil. Such a foil layer can be prepared with holes located in a pattern that matches the position or positions of the desired finished nanopores. The foil can then be used as a protective layer between the nanometric material being processed by incoming defect-generating particles and the source of the incoming defect-generating particle.

In an alternative embodiment, a highly focused particle beam, e.g., a focused gallium ion beam, or other focused beam such as an electron beam, at suitable energy as described above, can be directed specifically to locations at which a nanopore nucleation site is to be produced in the formation of a nanopore, in a sequential manner. This sequential site-irradiation technique eliminates the need for a physical mask while at the same time producing defects with nanometer accuracy in position.

The source of the particles to be employed for forming a nanopore nucleation site need not be dry and instead can be provided in an aqueous solution, or other suitable environment. For example, an aqueous solution can be provided as a 7% (w/w) solution of uranyl acetate in distilled water. Because a small percentage of any uranium solution is $Ur^{238}$, the solution will emit alpha particles for impinging on a material placed in the solution.

Referring now to FIG. 3D, in the second step of the process, there is controllably formed a nanopore at the nanopore nucleation site. In this nanopore formation step, the nucleation site 44 is perturbed in a manner that controllably produces a nanopore without damaging the nanometric material surrounding the nucleation site. This nanometric material surrounding the nucleation site is herein defined as that nanometric material that was not disturbed by the nucleation site-generating process of the first step in the method.

In one example process, as shown in FIG. 3D, a beam 45 of particles 47 having an energy that is below the energy threshold for knock-on damage in the undisturbed nanometric material, i.e., below the threshold for removal of bulk atoms from the nanometric material, is directed normal to the plane of atoms 32 of the nanometric material. These energetic particles 47 controllably remove only those edge atoms 50 at the circumference, or perimeter, of the nanopore nucleation site 44 while retaining the integrity of the remaining nanometric material by not removing bulk atoms from the interior locations of the nanometric material that are not at the nanopore nucleation site.

As shown in FIG. 3D, an incoming particle 52 striking the edge of the nucleation site 44 can remove an edge atom 50 at the periphery of the site, while an incoming particle 54 that strikes the nanometric material at a location away from the nanopore nucleation site does not cause removal of a bulk atom from the interior of the nanometric material. As the irradiation of the nanometric material is continued, additional edge atoms are removed at the periphery of the nucleation site, while away from the nucleation site the nanometric material remains intact and bulk atoms are not removed. Absent any source of atoms to fill in those edge atoms that are removed, a nanopore develops at the nanopore nucleation site. The nanopore geometry therefore is directly influenced by the evolving state of edge atom removal at the nanopore nucleation site. The nanopore may be generally circular, but can be any selected geometry, and can include asperities or other non-continuous geometric features.

The diameter of the nanopore increases in direct proportion to the dose of removal environment, e.g., electrons or ions per unit area, thus offering very accurate control of the area of the nanopore. Given that the nanopore can have an irregular geometry, e.g., that is non-circular, the term diameter can refer to, e.g., the largest extent across the nanopore. Beam irradiation of the forming nanopore can be controllably stopped when the nanopore reaches the desired size. As shown in FIG. 3E, formation of a nanopore 55 is then completed in the nanometric material 30. The nanopore can be characterized by a diameter or largest extent between edges, that ranges from, e.g., between about 3 Å and about 1000 Å.

FIG. 5A schematically presents an example of the resulting nanopore 70 produced in a nanometric material 16 that is self-supported and that extends across an opening in a frame 18 on a substrate 20. FIG. 5B similarly schematically presents an example of an array of nanopores 75 produced simultaneously in a self-supported nanometric material 24, on a frame 28 and substrate 29 with distinct selected regions of nanometric material 76 in which nanopores are provided in a controllable fashion.

An ion beam, electron beam, or other suitable beam of energy that can be directed to the plane of a nanometric material can be employed in this nanopore formation step. For many applications, a low-energy ion beam that is unfocused on the scale of the nanopore can be preferred, given the production of nanopore nucleation sites also by an ion beam. An all-ion beam process enables large-scale production in an efficient, practical manner, with the entire process conducted in a single inexpensive apparatus in which large device areas and/or many devices can be processed in parallel.

Because the beam is employed in the nanopore formation step to selectively remove atoms only from the edge of the nanopore nucleation site, the energy of the incident beam is tuned specifically to this condition. Particles of the beam therefore preferably are characterized by an energy that is greater than that required to remove an atom at the edge of the nanopore but less than that which would remove a bulk atom from the interior of the material. To quantify this condition, there can be defined an edge atom displacement energy, $E_d^{edge}$, given as the energy required to remove an atom from the edge of a nanometric material. An incident particle beam should have an energy such that the maximum transmitted energy, $T_m$, in a single scattering event, as expressed in Expression (1) above, is set as:

$$E_d^{edge} < T_m < E_d^{bulk} \quad (4)$$

The value of $E_d^{edge}$, if unknown, can be estimated by summing the bonding energies for an atom at an edge of the lattice of the nanometric material, using, e.g., tabulated values. Considering, e.g., a graphene edge atom, which on average has two bonds to the bulk lattice, then $E_d^{edge} \approx 6.4$ eV×2=13 eV, a value that is reasonably close to the experimentally-measured value of 14.1 eV. Based on this value, if there is employed an energetic beam having an energy such that $T_m \approx (E_d^{bulk} + E_d^{edge})/2 = (19+13)/2 = 16$ eV, then only the atoms at the edge of a nanopore nucleation site in graphene will be removed. This value can be further tuned empirically to optimize the removal of atoms at the edge of a nanopore nucleation site without creating additional defects in the bulk lattice.

Once one has selected an appropriate energy for the beam then the rate of edge atom removal can be measured, either during irradiation if a detector is available in situ to detect the particles transmitted through the membrane or on several samples with stepwise increases in dose followed by imaging to determine the number of atoms removed per incident particle dose. The irradiation of a nanopore nucleation site by the energetic beam is continued until a sufficient beam particle dose has removed a sufficient number of edge atoms at the nanopore nucleation site to form a nanopore of selected size. For example, given the use of an 80 keV electron beam to form nanopores at nanopore nucleation sites in graphene, then an electron beam fluence of about $3 \times 10^3$ e$^-$/Å$^2$/s, can form a nanopore having a 20 Å radius in about two hours. Thus, the energetic beam dose can be a priori selected to produce a corresponding nanopore size.

As an alternative to dry beam processing, if it is desirable to maintain a nanometric material in a liquid solution, a selected solution can be employed to preferentially react with nanopore nucleation sites on the nanometric material. For example, given a graphene material, then nitric acid or other solution chemistries that are known to preferentially react with disturbed nanometric sites, such as non-six-membered carbon ring lattice structures, or the edges of a graphene lattice, can be employed to form a nanopore at a nanopore nucleation site in the graphene. Continued chemical exposure with, for example, nitric acid, can effect controlled removal of atoms from only the disturbed site and the subsequently-formed nanopore edge, while leaving the rest of the undisturbed graphene intact. Such chemical treatment can be preferred for feed-back control of the nanopore size by monitoring ionic flow through the growing nanopore in the sheet of graphene. Once a nanopore of selected size has been produced, the reaction can be terminated by, e.g., introduction of a neutralizing base species, such as KOH, into the solution, or provision of another basic solution. Alternatively, an automatically operative set of solutions can be employed, e.g., with an acid on one side of the nanometric material, to etch a nanopore in the material, and a basic solution on the other side of the nanometric material to neutralize the acid and stop the nanopore formation process. The ratio of acid molarity to basic molarity can here be specified to determine the nanopore size at which etching ceases.

It is found that like nanopore nucleation site formation, nanopore formation itself can be influenced by temperature. For example, during irradiation at room temperature, atoms can diffuse around the inside edge of the nanopore, affecting the overall nanopore shape. Controlling the temperature of the nanometric material during irradiation can therefore be preferred to enable an ability to increase or decrease the amount of material diffusion that occurs at the evolving nanopore edge, and thus control the shape of the nanopore. For many applications, a nanopore formation temperature of between about 78 K and less than about 300 K or less than about 200 K, can be preferable.

The shape of an evolving nanopore can also be controlled by using a focused electron beam, such as that in a scanning transmission electron microscope (STEM), and slowly moving the focused beam area to etch away only particular portions of the edge of the nanopore. The nanopore shape can also be modified by exposing the nanometric material to an increased temperature after irradiation to adjust the shape, e.g., roundness, or other aspect of the nanopore.

For many applications, it can be preferable to empirically characterize the nanopore formation process so that a nanopore diameter specified a priori can be produced with a corresponding beam dose. In one method for determining such, there is experimentally determined the nanopore size that results as a function of total dose, e.g., total electron dose. For example, for the nanometric material graphene, the edge of graphene is characterized by a distinct defocused fringe pattern in a transmission electron micrograph (TEM). The radius of a nanopore in a graphene region can be determined by selecting the center of the nanopore and integrating the image intensity over azimuthal angles as a function of radius, dividing by the circumference at that radius as a normalization. The point of inflection of the defocused edge fringe can be identified as the average radius of the nanopore.

For many applications, it can be convenient to image the nanopore during its formation to obtain the requisite radius data. For example, given nanopore formation in graphene, TEM exposure to a defocused electron beam at an energy of about 80 keV enables formation of a nanopore at a nanopore nucleation site and provides imaging capabilities for real-time imaging of the nanopore evolution. Similarly, the nitric acid-based nanopore formation process described above enables feedback control provided by the monitoring of ionic current flow through an evolving nanopore.

However nanopore radius data is collected, once such is available, there can be determined the correlation between dose and nanopore radius for given nanometric material and beam irradiation conditions and temperature, such that an essentially automated approach to formation of a nanopore of prespecified diameter can be enabled. The circumference of a nanopore can be specified as increasing linearly with dose as nanopore edge atoms are removed. For a circular nanopore, this can be specified for the nanopore radius, r, as r=Md where d is the dose, e.g., in electrons/unit area, and where M is the measured constant of proportionality.

With this specification for obtaining a selected radius, there is enabled the ability to form large populations of monodisperse nanopores in a selected nanometric material. Such nanopore populations can be particularly important for, e.g., microfluidic applications such as filtering, molecular analysis, and chemical reactions. In general, to enable such applications, the nanometric material is impermeable to a species that is intended to be passed through the nanopores. The nanopores can be formed in an array that is ordered or in a random configuration, and that is monodisperse in diameter. The term monodisperse is herein meant to refer to a monodispersity in diameter of a plurality of nanopores in a population of nanopores, with a variation of about ±30%. This monodispersity can be achieved in a nanometric material with the two-step nanopore formation method to produce, e.g., a plurality of nanopores each having a diameter of, e.g., no greater than about 10 nm, e.g., no greater than about 4 nm, in a population of, e.g., about 1000 nanopores/$cm^2$ having a monodispersity in diameter with a variation of about ±30%. In a further example, this monodispersity can be achieved in a nanometric material for a selected number of nanopores, e.g., at least about 50 nanopores, each having a diameter of, e.g., no greater than about 10 nm, e.g., no greater than about 4 nm, having a monodispersity in nanopore diameter with a variation of about ±30%.

This nanopore formation control can be easily exploited to repeatedly and reliably form populations of nanopores that meet specific requirements for a range of applications. Whether one nanopore, a small plurality of nanopores, or a large population of nanopores is needed, the two step nanopore formation process enables atomic-scale control of the nanopore formation process.

Example 1

Formation of a 20 Å Nanopore in Graphene

The nanometric material graphene was synthesized by chemical vapor deposition on a 25 μm-thick polycrystalline copper substrate (Aesar). The substrate was annealed at low pressure under continuous $H_2$ flow at 1000° C. for ~10 minutes, exposed to an additional flow of $CH_4$ for ~10 min at 1000° C. to grow the graphene, and then allowed to cool back to room temperature under continuous gas flow, requiring about 2 hours. After growth, the graphene was transferred to gold TEM grids covered in a thin amorphous carbon film with regular arrays of micron scale holes (Quantifoil, Au 1.2/2.0). A drop of deionized water was placed on the TEM grid and then the grid was placed on the graphene, which was pulled into contact with the graphene by the receding interface from the water droplet. The copper was then etched away from below by floating the structure on top of $FeCl_3$ copper etchant (Transene). Once etched, the sample was then floated in 1N HCl to remove residual iron from the $FeCl_3$ and then floated in three rinses of deionized water to remove any residual salt, and dried in dry nitrogen.

At this point, several of the structures still contained variable amounts of surface contamination that likely formed during the growth procedure, so bake-out of the contamination was conducted. The TEM grids were transferred to a stainless steel UHV chamber that was just baked to 400° C., evacuated to <$10^{-8}$ torr, and then baked overnight at 300° C. The final pressure in the chamber after bake-out was ~$5 \times 10^{-9}$ torr. The structures were then stored in this chamber under UHV at room temperature until use.

To produce isolated nanopore nucleation sites in the graphene lattice, the structures were transferred to an ion sputtering system capable of irradiating samples at various temperatures with a known dose of ions under UHV conditions. The beam fluence was calibrated by measuring the count rate of the beam limited by an aperture of known size. Each structure was inserted through a load-lock mechanism and then cooled to the base temperature of 148 K. The residual pressure in the chamber was <$10^{-9}$ torr, and the residual partial pressures of species up to 100 AMU were monitored with an in situ residual gas analyzer (Ametek) to ensure that there were no detectable hydrocarbons, water, or other reactive species in the chamber during irradiation.

To produce nanopore nucleation sites in the graphene, the positive argon ion beam was pulsed with a duty cycle of 500 msec on-500 msec off until the structure reached the desired dose that was computed to produce the requisite disruption to the graphene, here $1\times10^{13}$ Ar$^+$/cm$^2$ at 3 keV. The sample was cooled to 149 K to reduce the probability of diffusion of atoms on the surface of the graphene, thus preventing atom movement from immediately repairing newly-formed nanopore nucleation sites in the lattice. Theoretically, each ion that transits the graphene has the ability to remove one or two atoms from the lattice, and the sputter yield for an argon ion at 3 keV on graphene is estimated to be of the order 0.5 carbon atoms removed per incident argon ion. After ion beam exposure to form nanopore nucleation sites was complete, the structure was then warmed back to 300 K and transferred to a small UHV chamber for storage.

The structure was then transferred to a transmission electron microscope (TEM) for controllably producing a nanopore. With the TEM, a single crystalline grain of graphene was identified using selected area diffraction, and the grain was verified as single-layer from relative diffraction peak intensities at 0° tilt. A selected region in the grain at which an ion-beam induced nanopore nucleation site existed was then continuously irradiated by a parallel, 80 keV electron beam, and images of the process were acquired at 30 or 60 second time intervals. The nanometric material structure was nominally maintained at room temperature within the electron microscope. The irradiation was periodically stopped as the nanopore diameter grew, to verify the control of the process. At an electron beam fluence of $3\times10^3$ e$^-$/Å$^2$/s, it was found that a nanopore of 20 Å radius was formed in about two hours.

Before and after the electron beam irradiation, the electron beam current was measured with a Faraday cup integral to the structure holder (Gatan single-tilt holder), attached to a pico-ammeter (Keithley 2400), and the beam area was measured directly from an image of the graphene grain irradiation area, which was limited by the condenser aperture. The largest contribution to systemic error is likely the beam current measurement, due to backscattering and secondary electron loss out of the 0.49 steradians of exit angle subtended by the entrance to the Faraday cup.

All other systematic biases were estimated to contribute <1% error to cross section measurements. Residual pressure was less than $1.3\times10^{-7}$ torr, and a liquid nitrogen anti-contamination device in close proximity to the structure protected it from contamination and residual water vapor in the column during electron irradiation. Objective lens aberrations were corrected to 3rd order using a post objective hexapole corrector (CEOS), aligned to have $C_1\cong+300$ Å, $C_3\cong-=-1$ µm, and all other aberration coefficients minimized. Images were zero-loss filtered to ~1 eV about the primary energy of 80 keV using the in-column omega filter to improve high-resolution phase contrast by removing the inelastic electrons. Micrographs were collected on a Gatan Ultrascan 4k camera or a TIVPS 4k camera at a nominal instrument magnification of 400-800 kX or camera length of 450 mm for selected area diffraction.

Example 2

Characterization of Graphene Nanopore Radius Correlation to Dose

To quantify the correlation between the radius of a nanopore in graphene as a function of dose of electrons employed to produce that nanopore radius, the two-step nanopore formation process of Example 1 was conducted, here with an ion beam dose of $1\times10^{13}$ Ar$^+$/cm$^2$ for producing nanopore nucleation sites in the graphene, and with an electron fluence of $3190\pm50$ e$^-$/Å$^2$/s for producing a nanopore at the sites. Sequential micrograph images containing multiple growing pores were obtained and analyzed by integrating the micrograph intensity over azimuthal angles as a function of radius, dividing by the circumference at that radius. The point of inflection of defocus at edge fringe was identified as the average radius of the nanopore.

Micrographs were drift corrected using a cross correlation algorithm and post-processed in ImageJ, with a low-pass filter to a 1.0 Å cutoff, adjusted to 8 bits of linear contrast about the mean intensity value, and cropped to the region of interest. The total exposure time in a particular micrograph was then determined by subtracting the image time stamp from the exposure start time. The exposure time multiplied by the beam fluence was then taken as the dose for a particular micrograph, as the beam current varied by <2% during the course of the experiment.

Figure 6A:
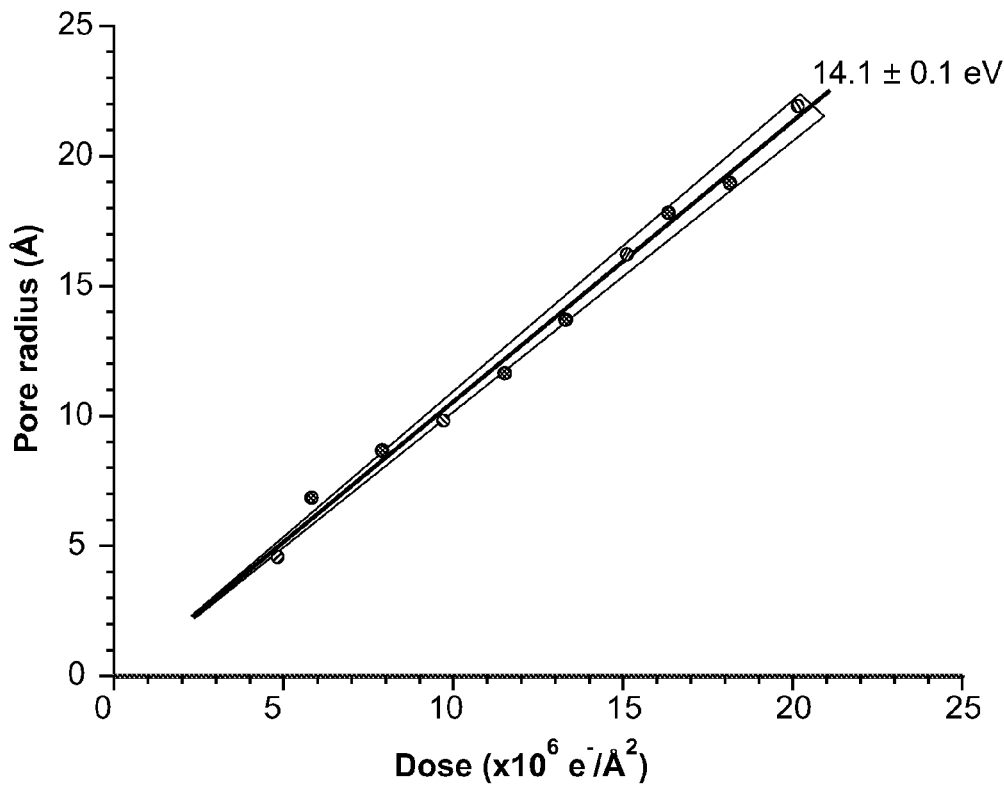
FIG. 6A is a plot of average nanopore radius as a function of electron dose for five experimental nanopores.
Figure 6B:
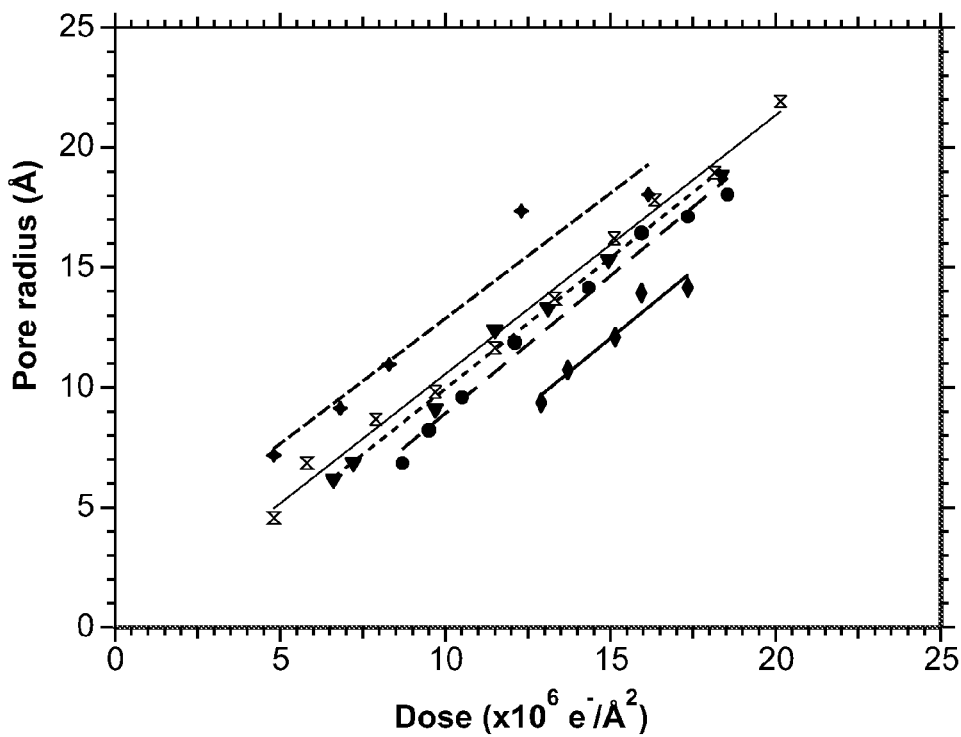
FIG. 6B is a plot of nanopore radius as a function of electron dose for each of the nanopores from which data was taken for the plot of FIG. 6A.

FIG. 6A is a plot of the resulting data for nanopore radius as a function of electron dose, where each data point is derived from the azimuthal integral of a nanopore image in a sequence of acquired images. Analysis on four additional nanopores produced under the same conditions resulted in measurement of random error in the slope of radius versus dose, and is identified by the grey region. The black line is a best linear fit to the trajectories for the total of five nanopores analyzed. FIG. 6B is a plot of each of the five sets of nanopore radius data, here provided separately.

Based on this experimental data, it is found that the circumference of the nanopore increased linearly with dose as nanopore edge atoms were removed. The average total cross section, $\sigma_e$, for removing the nanopore edge atoms was determined from the experimental data, based on the slope and the density of carbon atoms at the nanopore edge. The result is $8.9\pm0.4\times10^{-24}$ cm$^2$, where the error is the standard deviation from 5 measurements. Using conservative estimates of the systematic error in the measurement technique, the upper and lower bounds on this value are 9.4 and $7.5\times10^{-24}$ cm$^2$ respectively.

Example 3

High-Density Nanopore Formation in Graphene

Figure 7:
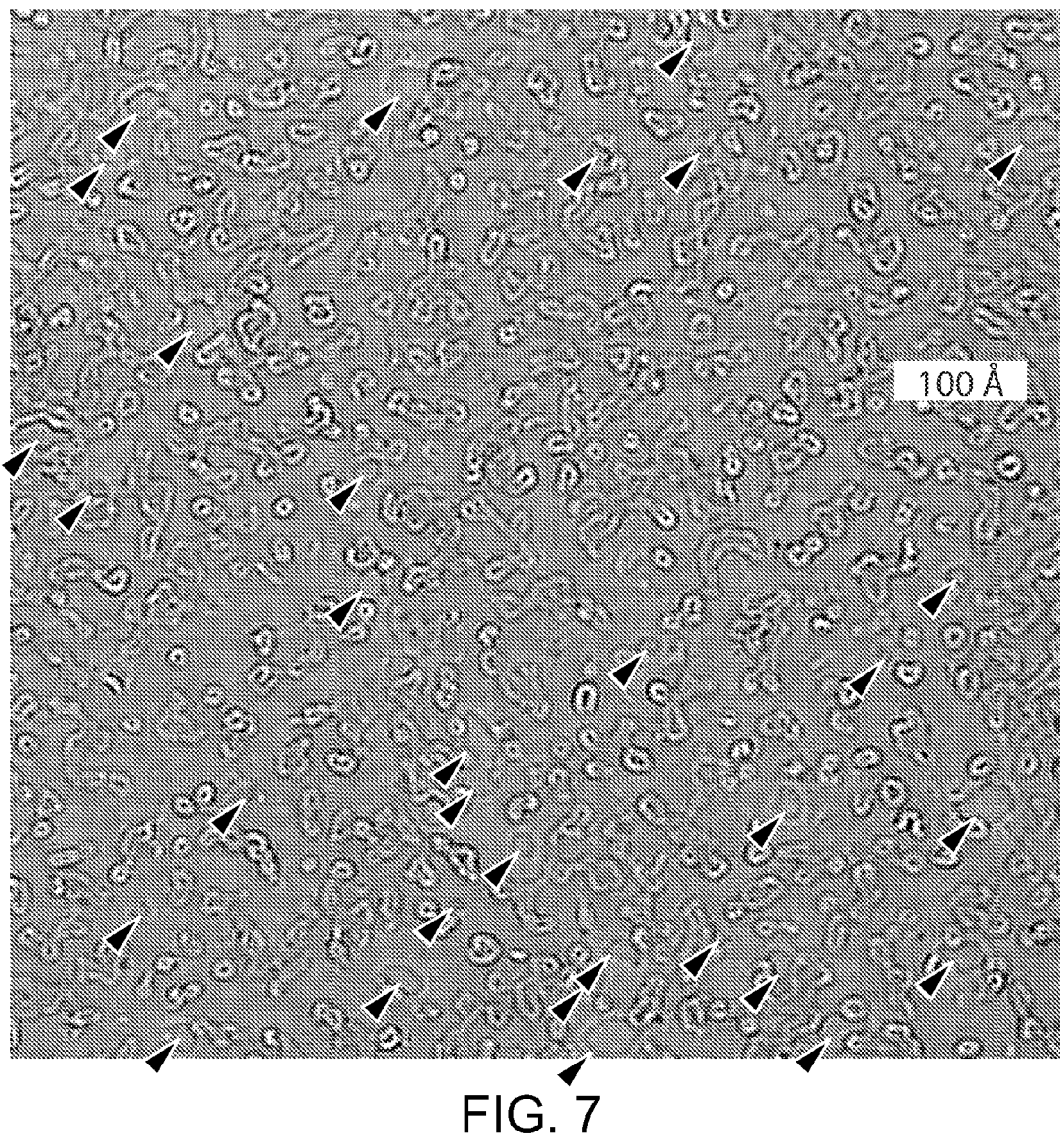
FIG. 7 is a an electron micrograph of a region of graphene in which an array of nanopores has been formed by the method of the flow chart of FIG. 1.

Following the process of Example 1, a graphene region of $6.27\times10^5$ Å$^2$ was exposed first to a 3 keV beam of argon ions to impose a dose of $1\times10^{13}$ Ar$^+$/cm$^2$ in the formation of nanopore nucleation sites, and then exposed to an electron beam to impose a dose of $9.7\times10^6$ e$^-$/Å$^2$ to form nanopores at the nucleation sites. FIG. 7 is a micrograph of the resulting structure, identifying 32 nanopores, as indicated by arrowheads. The locations of some of the smaller and larger nanopores in the image were determined by looking at preceding and subsequent images in a series of images. The resulting nanopore density corresponds to $5.1\times10^{11}$ nanopores/cm$^2$. This correlates with the ion beam dose of $1\times10^{13}$ Ar$^+$/cm$^2$ as each 3 keV Ar$^+$ having a probability of about 5% of nucleating a nanopore under these irradiation conditions.

Figure 8:
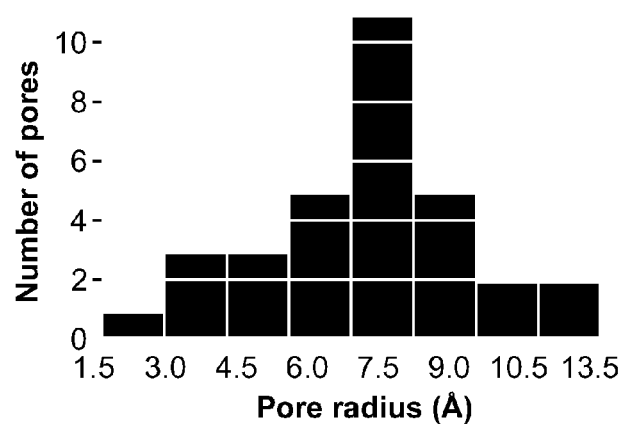
FIG. 8 is a plot of the distribution of nanopore radius for the electron micrograph of FIG. 7.

FIG. 8 is a plot of nanopore radius distribution for the nanopores shown in the image of FIG. 7. The nanopore radius distribution is found to be sharply peaked. This data demonstrates that the nanopore formation process is particularly effective at producing monodisperse nanopores. Monodisperse is here defined as a distribution in radius of ±30%.

Example 4

Comparative Example of Electron Beam Irradiation without Nanopore Nucleation Site Production An experiment was conducted to confirm that nanopore nucleation site synthesis is required to enable nanopore formation in accordance with the method described above. In the control experiment, a graphene region of 6.27×10$^5$ Å$^2$ was prepared in the manner of Example 1, corresponding to the graphene region extent of Example 3. The synthesized graphene was exposed to an 80 keV electron beam to impose an electron dose of 9.7×10$^6$ e$^-$/Å$^2$ in the manner of Example 3. This electron beam energy meets the requirement of the two-step nanopore formation method in that 80 keV is lower than the required to remove bulk graphene atoms, in the interior region of the graphene material. No ion beam irradiation step to first form nanopore nucleation sites was conducted. After the electron beam dose was produced, the graphene was examined, and was found to include no nanopores. This confirms that without the formation of nanopore nucleation sites, the electron beam dose does not form nanopores.

This description and examples demonstrate that the nanopore nucleation and formation process provides an elegantly uncomplicated, efficient, and repeatable process that can be implemented on a large scale over large areas and many devices. Many applications requiring mass-production of nanopores can therefore be implemented in a practical manner and reasonable cost.

It is recognized, of course, that those skilled in the art may make various modifications and additions to the processes of the invention without departing from the spirit and scope of the present contribution to the art. Accordingly, it is to be understood that the protection sought to be afforded hereby should be deemed to extend to the subject matter of the claims and all equivalents thereof fairly within the scope of the invention.

We claim:

1. A method of forming a nanopore in a nanometric material, the method comprising:

forming a nanopore nucleation site in a nanometric material, the nanometric material having a thickness that is less than about 5 nanometers, the nanopore nucleation site being formed at a location of the nanometric material that is interior to lateral edges of the nanometric material by directing a first energetic beam, selected from the group consisting of ion beam and neutral atom beam, at the interior location with a beam energy that is at least that beam energy which provides at the nanometric material a bulk atom displacement energy of $E_d^{bulk}$, that can remove bulk atoms from the nanometric material, for a first time duration that imposes a first beam dose which causes removal of no more than five interior bulk atoms from the interior location to produce at the interior location a nanopore nucleation site having a plurality of edge atoms; and forming a nanopore at the nanopore nucleation site by directing a second energetic beam, selected from the group consisting of electron beam, ion beam, and neutral atom beam, at the nanopore nucleation site with a beam energy that is less than that beam energy which provides at: the nanometric material a bulk atom displacement energy of $E_d^{bulk}$, to thereby remove edge atoms at the nanopore nucleation site but not remove bulk nanometric material atoms that are not at the nanopore nucleation site.

2. The method of claim 1 wherein the second energetic beam is directed at the nanopore nucleation site for a second time duration that imposes a second beam dose which causes removal of a plurality of edge atoms to form a nanopore in the nanometric material having a diameter less than about 1000 Å.

3. The method of claim 1 wherein the nanometric material is selected from the group consisting of graphene, few-layer graphene, fluorographene, graphane, and graphene oxide.

4. The method of claim 1, wherein the nanometric material is selected from the group consisting of hexagonal-BN, mono-atomic glasses, $MoS_2$, $WS_2$, $MoSe_2$, $MoTe_2$, $TaSe_2$, $NbSe_2$, $NiTe_2$, and $Bi_2Te_3$.

5. The method of claim 1 further comprising first disposing on the nanometric material a patterned masking material that includes openings through which the energetic beams can be directed at the nanometric material.

6. The method of claim 1 wherein the first energetic beam comprises an ion beam selected from the group consisting of argon, gallium, neon, hydrogen/proton, and helium ion beams.

7. The method of claim 1 wherein the first energetic beam and the second energetic beam each are ion beams.

8. The method of claim 1 wherein the first energetic beam is an ion beam and the second energetic beam is an electron beam.

9. The method of claim 1 wherein forming a nanopore comprises forming a nanopore having an extent that is between about 3 Å and about 1000 Å.

10. The method of claim 1 further comprising detecting, during direction of the second energetic beam to the nanometric material, beam particles that are transmitted through a forming nanopore, and controlling the second energetic beam in response to the detection to form a nanopore of a selected extent.

11. The method of claim 1 further comprising maintaining the nanometric material at a temperature no greater than about 300 K when the first energetic beam is directed at the nanometric material.

12. The method of claim 11 further comprising maintaining the nanometric material at a temperature no greater than about 200 K when the first energetic beam is directed at the nanometric material.

13. The method of claim 1 further comprising maintaining the nanometric material at a temperature no greater than about 300 K when the second energetic beam is directed at the nanometric material.

14. The method of claim 13, further comprising maintaining the nanometric material at a temperature no greater than about 200 K when the second energetic beam is directed at the nanometric material.

15. The method of claim 1 wherein forming a nanopore nucleation site comprises forming an array of nanopore nucleation sites, and wherein forming a nanopore at the nanopore nucleation site comprises forming a nanopore at each site in the array of nanopore nucleation sites.

16. The method of claim 15 wherein forming an array of nanopore nucleation sites comprises forming a nanopore nucleation site array having a density of at least about 1000 nanopore nucleation sites/cm$^2$, and wherein forming a nanopore comprises forming a nanopore at each site in the array of nanopore nucleation sites.

17. The method of claim 1 further comprising a first step of disposing the nanometric material on a support structure for processing by the first and second energetic beams.

18. The method of claim 17 further comprising a first step of synthesizing the nanometric material and transferring the synthesized material to the support structure.

19. The method of claim 17 wherein the support structure includes an aperture across which the nanometric material extends.

20. The method of claim 19 wherein the support structure comprises a transmission electron microscopy grid.

* * * * *